United States Patent
Menon Gopalakrishna et al.

(10) Patent No.: US 9,179,881 B2
(45) Date of Patent: Nov. 10, 2015

(54) PHYSICS BASED IMAGE PROCESSING AND EVALUATION PROCESS OF PERFUSION IMAGES FROM RADIOLOGY IMAGING

(75) Inventors: Prahlad Menon Gopalakrishna, Pittsburgh, PA (US); Mark Doyle, Wexford, PA (US)

(73) Assignee: Carnegie Mellan University, Pittsburgh, PA (US)

( * ) Notice: Subject to any disclaimer, the term of this patent is extended or adjusted under 35 U.S.C. 154(b) by 0 days.

(21) Appl. No.: 13/525,298

(22) Filed: Jun. 16, 2012

(65) Prior Publication Data

US 2012/0323118 A1    Dec. 20, 2012

(51) Int. Cl.
*A61B 6/00*    (2006.01)
*A61B 8/06*    (2006.01)
*A61B 8/00*    (2006.01)
*A61B 8/08*    (2006.01)

(52) U.S. Cl.
CPC .......... *A61B 6/463* (2013.01); *A61B 6/481* (2013.01); *A61B 6/507* (2013.01); *A61B 6/5217* (2013.01); *A61B 6/5229* (2013.01); *A61B 8/06* (2013.01); *A61B 8/065* (2013.01); *A61B 8/463* (2013.01); *A61B 8/5223* (2013.01)

(58) Field of Classification Search
CPC ........ A61B 6/463; A61B 6/481; A61B 6/507; A61B 6/5217; A61B 6/5229; A61B 8/5223; A61B 8/06; A61B 8/065; A61B 8/463
USPC .......................................................... 600/431
See application file for complete search history.

(56) References Cited

U.S. PATENT DOCUMENTS

| | | |
|---|---|---|
| 6,628,743 B1 | 9/2003 | Drummond et al. |
| 6,745,066 B1 | 6/2004 | Lin et al. |
| 6,904,306 B1 | 6/2005 | Wu et al. |
| 7,698,234 B2 | 4/2010 | Breeuwer |
| 7,747,308 B2 | 6/2010 | Hundley et al. |
| 7,805,181 B2 | 9/2010 | Breeuwer |
| 8,157,742 B2 | 4/2012 | Taylor |
| 2005/0002547 A1* | 1/2005 | Torre-Bueno ............. 382/128 |
| 2008/0058636 A1 | 3/2008 | Caravan et al. |
| 2008/0108894 A1 | 5/2008 | Elgavish et al. |
| 2009/0005672 A1 | 1/2009 | Sugiura |
| 2009/0105582 A1* | 4/2009 | Dougherty et al. ......... 600/420 |

(Continued)

OTHER PUBLICATIONS

Mines et al., Fully Automated Motion Correction in First-Pass Myocardial Perfusion MR Image Sequences, IEEE Transactions on Medical Imaging, vol. 27, No. 11, Nov. 2008.*

(Continued)

*Primary Examiner* — Bo J Peng
(74) *Attorney, Agent, or Firm* — Tucker Arensberg, P.C.

(57) ABSTRACT

A process and a system for assisting a clinician in identification and evaluation of perfusion characteristics of an organ are disclosed. The process and system may be used to extend clinical diagnosis capabilities by augmenting the ability to analyze perfusion images acquired from a radiology imaging modality through the use of the quantification technology as described. Classification of perfusion characteristics of a region of interest is facilitated through the use of a quantitative spatial perfusion characteristics map. The map is generated by a computing device which applies at least one physics-based image processing technique. This map is displayed on a clinician device for review by the clinician to assist in the spatial identification of perfusion abnormalities.

30 Claims, 5 Drawing Sheets

(56) References Cited

U.S. PATENT DOCUMENTS

| | | |
|---|---|---|
| 2009/0238424 A1 | 9/2009 | Arakita et al. |
| 2010/0067767 A1 | 3/2010 | Arakita et al. |
| 2010/0204572 A1 | 8/2010 | Kalafut et al. |
| 2012/0059246 A1 | 3/2012 | Taylor |
| 2012/0082352 A1 | 4/2012 | Hundley et al. |

OTHER PUBLICATIONS

Franiel et al., Differentiation of Prostate Cancer From Normal Prostate Tissue: Role of Hotspots in Pharmacokinetic MRI and Histologic Evaluation, AJR 2010; 194:675-681, Mar. 2010.*
Cordier et al., Evaluation of three inverse problem models to quantify skin microcirculation using diffusion-weighted MRI.*
Le et al., Simultaneous Myocardial Strain and Dark-Blood Perfusion Imaging Using a Displacement-Encoded MRI Pulse Sequence, Magnetic Resonance in Medicine 64:787-798, Published online Jun. 11, 2010.*
Ozarslan et al., Generalized Scalar Measures for Diffusion MRI Using Trace, Variance, and Entropy, Magnetic Resonance in Medicine 53:866-876, 2005.*
Liu et al., Intervertebral Disk Degeneration Related to Reduced Vertebral Marrow Perfusion at Dynamic Contrast-Enhanced MRI, AJR:192, Apr. 2009.*
Meng et al., Characterizing the Diffusion/Perfusion Mismatch in Experimental Focal Cerebral lschemia, Ann Neurol. Feb. 2004 ; 55(2): 207-212.*
Shen et al., Functional, perfusion and diffusion MRI of acute focal ischemic brain injury, J Cereb Blood Flow Metab. Oct. 2005; 25(10): 1265-1279.*
Jerosch-Herold, Michael, Quantification of Myocardial Perfusion by Cardiovascular Magnetic Resonance, Journal of Cardiovascular Magnetic Resonance, 2010, 12:57, accessible from: http://www.jcmr-online.com/content/12/1/57, last accessed on Feb. 21, 2014.
N.M. Wilke et al.., Magnetic Resonance First-Pass Myocardial Perfusion Imaging: Clinical Validation and Future Applications, J Magn Reson Imging, vol. 10, pp. 676-685, Nov. 1999.
Moriel H. Vandsburger et al., Emerging MRI Methods in Translational Cardiovascular Research, J. of Cardiovasc Trans Res, published online Mar. 31, 2011.
R.S. Tan and K.K. Chen, Coronary Artery Disease: Comprehensive Evaluation by Cardiovascular Magnetic Resonance Imaging, Ann Acad Med Singapore vol. 33, pp. 437-443, Jul. 2004.
G. Pilz et al., Clinical Applications of Cardiac Magnetic Resonance Imaging, Minerva Cardiology, vol. 57, pp. 299-313, Jun. 2009, Abstract.
D.S. Berman et al., Roles of Nuclear Cardiology, Cardiac Computed Tomography, and Cardiac Magnetic Resonance: Assessment of Patients with Suspected Coronary Artery Disease, J Nucl Med, vol. 47, pp. 74-78, Jan. 2006.
J. Barkhausen et al., MRI in Coronary Artery Disease, Eur Radiol , vol. 14, pp. 2155-2162, Dec. 2004.
M. Doyle et al., The Impact of Myocardial Flow Reserve on the Detection of Coronary Artery Disease by Perfusion Imaging Methods: An NHLBI WISE Study, J Cardiovasc Magn Reson, vol. 5, pp. 475-485, Jul. 2003.
J.U. Fluckiger et al., Constrained Estimation of the Arterial Input Function for Myocardial Perfusion Cardiovascular Magnetic Resonance, Magn Reson Med, Mar. 28 2011.
M. Doyle et al., Prognostic Value of Global MR Myocardial Perfusion Imaging in Women wiht Supsected Myocardial Ischemia and No Obstructive Coronary Disease: Rueslts from the NHLBI-Sponsored WISE (Women's Ischemia Syndrome Evaluation) Study, JACC Cardiovasc Imaging, vol. 3, pp. 1030-1036, Oct. 2010.
M. Jerosch-Herold et al., Myocardial Blood Flow Quantification with MRI by Model-Independent Deconvulation, Med Phys, vol. 29, pp. 886-897, May 2002.
E. Kehr et al., Gadolinium-Enhanced Magnetic Resonance Imaging for Detection and Quantification of Fibrosis in Human Myocardium in Vitro, Int J Cardiovasc Imaging, vol. 24, pp. 61-68, Jan. 2008.
M. Jerosh-Herold et al., Magnetic Resonance Quantification of the Myocardial Perfusion Reserve with a Fermi Function Model for Constrained Deconvolution,Med. Phys. 25(1), Jan. 1998.
J. Trzasko et al., Highly Undersampled Magnetic Resonance Image Reconstruction via Homotopic Minimization, IEEE Transactions on Medical Imaging, col. 28, No. 1, Jan. 2009.
Emmanuel Candes et al., Enhancing Sparsity by Reweighted Minimization, Journal of Fourier Analysis and Applications, Dec. 2008, vol. 14, Issue 5-6, pp. 877-905.
Thomas Porter et al., Myocardial Perfusion Imaging with Contrast Ultrasound, accessible at: http://imaging.onlinejacc.org/cgi/content/full/3/2/176, JACC: Cardiovascular Imaging, vol. 3, No. 2, 2010.
Kondo, Myocardial Perfusion Imaging in Pediatric Cardiology, Abstract, Annals of Nuclear Medicine, vol. 18, No. 556, 2004. 7, 551.
Mahnken, Computed Tomography Imaging in Myocardial Infarction, Expert Rev Cardivasc Ther 9(2), 211-221 (2011).

* cited by examiner

PHYSICS BASED IMAGE PROCESSING AND EVALUATION PROCESS OF PERFUSION IMAGES FROM RADIOLOGY IMAGING

CROSS-REFERENCE TO RELATED APPLICATIONS

This application claims the benefit of an earlier-filed U.S. Provisional Application, entitled "Physics based image processing and evaluation techniques applied to diagnosis of left ventricular ischemia using cardiac MRI first-pass contrast perfusion imaging" having Serial No. 61/520,922, filed Jun. 17, 2011 and an earlier-filed International Application entitled "Physics Based Image Processing And Evaluation Process Of Perfusion Images From Radiology Imaging" having Serial No. PCT/US12/42834, filed Jun. 15, 2012. Serial No. PCT/US12/42834 also claims the benefit of the earlier-filed U.S. Provisional Application, entitled "Physics based image processing and evaluation techniques applied to diagnosis of left ventricular ischemia using cardiac MRI first-pass contrast perfusion imaging" having Ser. No. 61/520,922, filed Jun. 17, 2011.

FIELD OF THE INVENTION

The present invention relates to a process and system for quantification of tissue perfusion using radiology images. More particularly, the present invention is concerned with augmenting the ability to analyze perfusion images acquired from a radiology imaging modality through the use of the physics based perfusion quantification technology.

BACKGROUND OF THE INVENTION

Heart disease is the leading cause of death for both men and women in the United States. In 2006, 631,636 people died of heart disease and heart disease caused 26% of deaths—more than one in every four—in the United States. Every year, about 785,000 Americans have a first heart attack and other 470,000 Americans who already had one or more heart attacks have another attack. Coronary heart disease is the most common type of heart disease. In 2005, 445,687 people died from coronary heart disease and these numbers are on the rise. According to 2010 statistics, 1 in 3 Americans (36.9%) have some form of heart disease, including high blood pressure, coronary heart disease, heart failure, stroke, and other conditions. By 2030, approximately 116 million people in the United States (40.5%) will have some form of cardiovascular disease.

Between 2010-30, it is projected that the cost of medical care for heart disease (in 2008 dollar values) will rise from $273 billion to $818 billion, according to an American Heart Association policy statement published in Circulation: Journal of the American Heart Association. See Heidenreich P A, et al. Forecasting the future of cardiovascular disease in the United States: A policy statement from the American Heart Association Circulation (2011).

The coronary angiogram, also referred to as the catheterization examination, is regarded as the "gold standard" for diagnosis of coronary artery disease (CAD). However, the use of coronary angiograms expose over 2.7 million Medicare/Medicaid reimbursed Americans to the risks and result in costs of invasive diagnostic examination every year, whereas only about 61% of these patients require clinical intervention. See Patel M R et al., Low diagnostic yield of elective coronary angiography, N Engl J. Med. 2010 March 11; 362(10):886-95 (erratum as published at N Engl J Med. 2010 July 29; 363(5): 498).

Preliminary diagnosis of CAD is commonly performed using radiology imaging modalities such as contrast Dobutamine Stress Echocardiography (DSE), nuclear cardiology Single Photon Emission Computed Tomography (SPECT) and Cardiac Computed Tomography (Cardiac CT). While DSE primarily assesses wall motion, SPECT allows simultaneous determination of myocardial perfusion and wall motion at relatively low resolution, although it exposes the patient to ionizing radiation and does not offer the opportunity to distinguish between wall-thickening function and perfusion.

The current landscape of diagnostic tests for heart disease creates a need to implement a less expensive screening test with high negative predictive value in order to be the gate-keeper to an invasive examination or an interventional surgery and also to augment the decision making capability of the clinician for patients with low and medium Framingham risk scores. In turn, this facilitates improved healthcare for the individual patient and at significant healthcare cost savings for the population. First-pass perfusion image acquisitions from cardiac magnetic resonance imaging (CMR) is a low cost, no toxicity, high sensitivity, and high specificity imaging modality for cardiac perfusion diagnostics which has the potential to solve this problem.

CMR is a currently underutilized capital equipment with great untapped clinical potential, according to a clinically proven comparison of CMR with other imaging modalities, which has indicated higher sensitivity and specificity in detection of coronary artery disease compared with SPECT. See Cardiovascular magnetic resonance and single-photon emission computed tomography for diagnosis of coronary heart disease (CE-MARC): a prospective trial, Lancet, 2012 Feb. 4; 379(9814):453-60.

A recent survey of cardiologists in the American Heart Journal has indicated that most cardiologists were willing to enroll patients with at least moderate ischemia into a trial using initial non-invasive diagnosis in preference to advancing directly to invasive cardiac catheterization. When added to the recent prognostic data that a normal (AIR stress test provides, namely, <1% mortality at 3 years as shown in 1500 consecutive patients, this is a compelling cost-effective strategy which does not involve the use of cardiac catheterization or a nuclear laboratory. Accordingly, the use of CMR may avert unnecessary catheterizations by assessment of cardiac perfusion and function using CMR.

Thus, CMR is an appropriate "gate-keeper" to the catheterization laboratory which will provide the clinician with assistance in detecting perfusion abnormalities which may indicate a problem with a patient's cardiac health. Further, CMR may be used to assist the clinician in detecting, at an early stage, perfusion abnormalities which may indicate a problem with a patient's cardiac health. Accordingly, the use of CMR may save several millions of dollars in cardiology related hospitalization and interventional treatment; effectively curbing the $273 billion cost of medical care for heart disease in the US. In addition, the American College of Cardiology (ACC) and American Heart Association guidelines recognize CMR as the "gold standard" for a large and growing number of cardiac applications.

CMR is a versatile non-invasive and non-ionizing imaging modality and offers time resolved image data to evaluate cardiac function at rest and either vasolidation or pharmacological stress, allowing myocardial perfusion to be evaluated independently of wall-thickening function. There is a need in the art for a program to efficiently and economically disseminate this non-invasive, non-radioactive, and safe CMR technique, which would have obvious advantages to the community.

Gadolinium-diethyenetriaminepentaacetate, a non-nephrotoxic extravascular contrast agent, is used to increase T1 weighted tissue signal from the myocardium CMR imaging. Modern CMR scanners use pulse sequences capable of fast image acquisition to obtain temporally resolved short-axis multi-slice first-pass perfusion image acquisitions of the heart. Such contrast enhanced first-pass perfusion CMR can be repeated regularly without any adverse effects for the patient. See N. M. Wilke, et al., "Magnetic resonance first-pass myocardial perfusion imaging: clinical validation and future applications," J Magn Reson Imaging, vol. 10, pp. 676-85, November 1999. Time resolved perfusion imaging is important because it provides crucial information, aiding identification of a stress response which is not possible to obtain from traditional imaging modalities. Based on M. Doyle, et al., "The impact of myocardial flow reserve on the detection of coronary artery disease by perfusion imaging methods: an NHLBI WISE study," J Cardiovasc Magn Reson, vol. 5, pp. 475-85, July 2003, there is evidence to show that CMR is the only modality with the sensitivity to identify the extent of the vasodilatory response. They showed that non-time resolved nuclear SPECT imaging lost accuracy when the vasodilatory response was inadequate (affecting about 30% of patients), but that knowledge of the vasodilatory response could be incorporated to improve the detection of myocardium at risk using first pass contrast perfusion CMR.

However, the transient image data in first-pass contrast perfusion sequences contain a high amount of dynamic information and pixel-level or voxel-level noise, making it difficult to evaluate visually without quantification. Further, quantification of myocardial perfusion is known to be challenging. See J. U. Fluckiger, et al., "Constrained estimation of the arterial input function for myocardial perfusion cardiovascular magnetic resonance," Magn Reson Med, Mar. 28, 2011. The method as described is capable of quantifying image data from perfusion sequences and subsequently providing a spatial map of perfusion conditions using physical contrast agent transport properties i.e. advection and diffusion. Previously, M. Doyle, et al., "Prognostic value of global MR myocardial perfusion imaging in women with suspected myocardial ischemia and no obstructive coronary disease: results from the NHLBI-sponsored WISE (Women's Ischemia Syndrome Evaluation) study," JACC Cardiovasc Imaging, vol. 3, pp. 1030-6, October 2010, showed that quantitative CMR perfusion is capable of detecting global (as opposed to regional) perfusion abnormalities which are unlikely to be seen in infarct imaging methods such as late Gadolinium enhancement CMR or on a coronary angiogram, possibly due to the small caliber of the arteries involved, which may represent an early stenosis condition prior to occlusion of the epicardial coronary arteries. Early diagnosis of suspected myocardial ischemia allow better patient management and prevention of progression to myocardial infarction and early cardiovascular death.

SUMMARY OF THE INVENTION

In an embodiment, a process and a system are provided for assisting a clinician in identification of perfusion characteristics of an organ through the use of a computing device. The process and system present significant improvements over the results that can be analyzed with prior art image post-processing technology, such as, for example, prior art technology for detecting heart muscle at risk of impending death.

In an embodiment, various methods of delivery of the process and system using a computing device are provided herein, such as, for example, in a local environment, a hosted environment, or a cloud computing environment (e.g., a software-as-a-service or SaaS solution).

In an embodiment, a process and a system are provided which utilize at least one physics-based image processing technique for the correlation of CMR first-pass perfusion signal intensity to the quality of perfusion based upon modeled normal perfusion characteristics by an advection and diffusion transport of blood from the left ventricle (LV) to the myocardium.

In an embodiment, a process and a system are provided for the rendering of quantitative spatial maps of cardiac tissue at risk of impending death (i.e., at-risk tissue) using non-invasively acquired first pass perfusion CMR scans.

In an embodiment, the process and system provide for a method of data representation of left ventricular myocardium of risk from perfusion data as a polar plot. The polar plot may assist the clinician in his or her diagnosis of the patient by performing tasks which include the following: (a) a classification task is to generate a map (i.e., a perfusion characteristics map) of probability of blockages in the coronary artery tree, (b) accurately detecting when the probability of blockage in a coronary artery exceeds some learned threshold impacting hemodynamics and perfusion (i.e. nutritional flow) to the myocardium, and (c) enabling the visualization of where in a coronary artery blockage has occurred, in 3D, based upon the quantitative diffusion parameter perfusion characteristics maps.

In an embodiment, the process and system can analyze perfusion data from other first-pass perfusion radiology imaging modalities besides CMR including, for example, ultrasound.

In an embodiment, the process and system may analyze perfusion characteristics of an organ which is the heart.

In an embodiment, the process and system may analyze perfusion characteristics of an organ other than the heart.

These embodiments and other embodiments of the present invention will become clear to those skilled in the art in view of the description of the best presently known modes of carrying out the invention and the applicability of the embodiments as described herein and as described in the figures, drawings, and appended claims.

DETAILED DESCRIPTION

A physics-based image processing technique and an evaluation process for diagnosis of perfusion abnormalities in non-invasively imaged tissue, for example in left ventricular myocardial ischemia, using radiology imaging is disclosed. Patient specific time series images of a tissue undergoing perfusion, for example first-pass perfusion CMR images, are analyzed for perfusion characteristics and displayed as perfusion characteristic maps of tissue at risk of impending death. In the case of cardiac tissue, patient-specific perfusion information may be correlated against myocardial function (i.e., wall motion and wall thickening) information in order to confirm suspicion of myocardial infarction or myocardial ischemia.

As described herein, this quantification technology may be used to extend a cardiologist's clinical diagnosis capabilities by assisting him or her with the identification of early signs of heart disease long before a patient experiences a myocardial infarction or a heart attack by augmenting the ability to analyze cardiac perfusion images acquired from radiology imaging modalities. It further presents a non-invasive pre-screening test with a high negative predictive value in order to be the gate-keeper to an invasive examination or interventional surgery for palliation of the condition causing the perfusion abnormality. In one example a first-pass perfusion CMR based analysis may be a gate-keeper to the invasive catheterization exam for identification and interventional correction of coronary blockages that cause ischemia or infarct formation, therefore reducing numbers of incidents of the significant unnecessary invasive procedures that have negative results (see Patel M R et al., Low diagnostic yield of elective coronary angiography. N Engl J Med. 2010 March 11; 362 (10):886-95. Erratum in: N Engl J. Med. 2010 July 29; 363 (5):498).

The process and system as described herein are performed by the computing device which has been programmed to process the steps as described below. The clinician device displays the visual representations generated by the computing device and these visual representations assist with spatial identification of perfusion abnormalities. The clinician device may be local or remote with respect to the location of the computing device.

In an embodiment, the computing device may be deployed in a local environment. In a related embodiment, the computing device may be the same device as the clinician device. In yet another related embodiment, the computing device may be a different device from the clinician device.

In another embodiment, the computing device may be deployed in a cloud computing environment. An example of a cloud computing environment is a Software as a Service (SaaS) environment. The computing device is located remotely from the clinician device. Because of the multi-tenant capability of the cloud computing environment, a plurality of clinician devices may access the computing device.

In still another embodiment, the computing device may be deployed in a hosted environment. The computing device is hosted by a third party. The computing device is in a remote location from the clinician device. A clinician device may access the computing device. The computing device may be dedicated for use by the clinician.

In one embodiment, a process is disclosed for assisting a clinician in identification of perfusion characteristics of an organ comprising the steps of:
 a. Acquiring a perfusion sequence comprising a plurality of two-dimensional image slices and a time series for each of said two-dimensional image slices by using a radiology imaging modality for contrast-enhanced perfusion imaging of said organ, wherein said plurality of two-dimensional image slices comprises a three-dimensional volume image,
 b. Retrieving said perfusion sequence from said radiology imaging modality using a computing device,
 c. Applying in-plane motion correction using said computing device to align position of said organ using said time series for each of said image slices,
 d. Cropping a first region of interest of said contrast-enhanced perfusion images using said computing device, wherein said first region of interest comprises a first plurality, of pixels or voxels representing said organ,
 e. Segmenting out at least one additional region of interest from said first region of interest by applying a standard algorithm, wherein said additional region of interest is within said first region of interest,
 f. Classifying said perfusion characteristics of said additional region of interest by characterizing a plurality of observed perfusion uptake curves for said additional region of interest by applying at least one physics-based image processing technique for producing at least one characteristic map of said perfusion characteristics using user-defined criteria or default criteria, wherein said characteristic map defines at-risk and normal perfusion areas, using said computing device, and
 g. Displaying at least one visual representation of said perfusion characteristics of said organ on a clinician device for review by said clinician to assist in spatial identification of perfusion abnormalities in said perfusion characteristics, wherein said visual representation is a two-dimensional visual representation or a three-dimensional visual representation.

Figure 1:
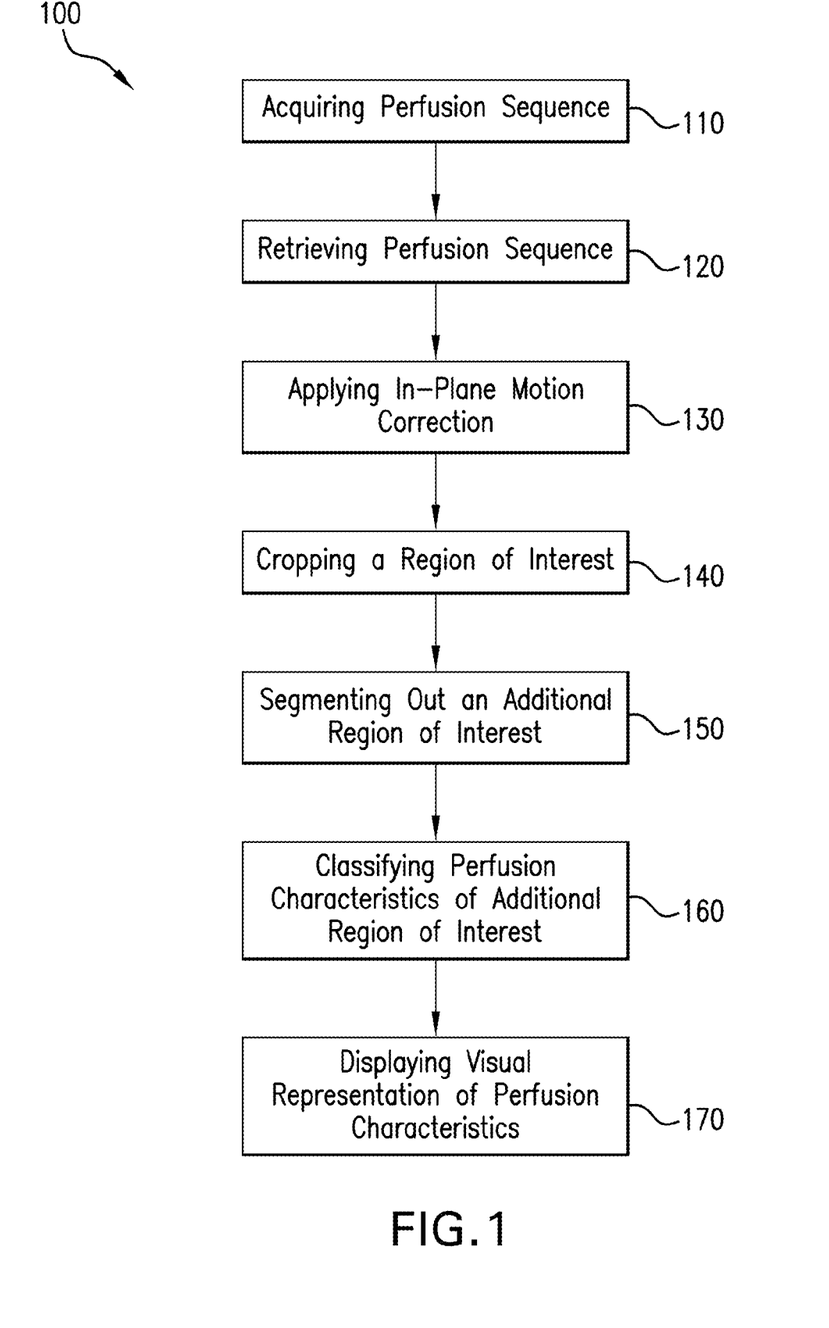
FIG. 1 illustrates an overview of the process for assisting a clinician in identification of perfusion characteristics of an organ.

In an embodiment, FIG. 1 provides an overview of the embodiment as described above in the form of a flowchart, namely, a process for assisting a clinician in identification of perfusion characteristics of an organ is provided as shown by reference numeral 100. The process occurs by way of the following steps as illustrated (and described in more detail herein): (1) acquiring a perfusion sequence 110, (2) retrieving the perfusion sequence 120, (3) applying in-plane motion correction 130, (4) cropping a region of interest 140, (5) segmenting out an additional region of interest 150, (6) classifying perfusion characteristics of additional region of interest 160, and (7) displaying a visual representation of perfusion characteristics 170. In another embodiment, there may be more than one region of interest which is segmented out.

In an embodiment, a system is disclosed for assisting a clinician in identification of perfusion characteristics of an organ, comprising:
 a. A radiology imaging modality for acquiring a perfusion sequence comprising a plurality of two-dimensional image slices and a time series for each of said two-dimensional image slices by using a radiology imaging modality for contrast-enhanced perfusion imaging of said organ, wherein said plurality of two-dimensional image slices comprises a three-dimensional volume image, and
 b. A computing device for retrieving said perfusion sequence from said radiology imaging modality using a computing device, applying in-plane motion correction using said computing device to align position of said organ using said time series for each of said image slices, cropping a first region of interest of said contrast-enhanced perfusion images using said computing device, wherein said first region of interest comprises a first plurality of pixels or voxels representing said organ, segmenting out at least one additional region of interest from said first region of interest by applying a standard algorithm, wherein said additional region of interest is within said first region of interest, classifying said perfusion characteristics of said additional region of interest by characterizing a plurality of observed perfusion uptake curves for said additional region of interest by applying at least one physics-based image processing technique for producing at least one characteristic map of said perfusion characteristics using user-defined criteria or default criteria, wherein said characteristic map defines at-risk and normal perfusion areas, using said computing device, and displaying at least one visual representation of said perfusion characteristics of said organ on a clinician device for review by said clinician to assist in spatial identification of perfusion abnormalities in said perfusion characteristics, wherein said visual representation is a two-dimensional visual representation or a three-dimensional visual representation.

Figure 2:
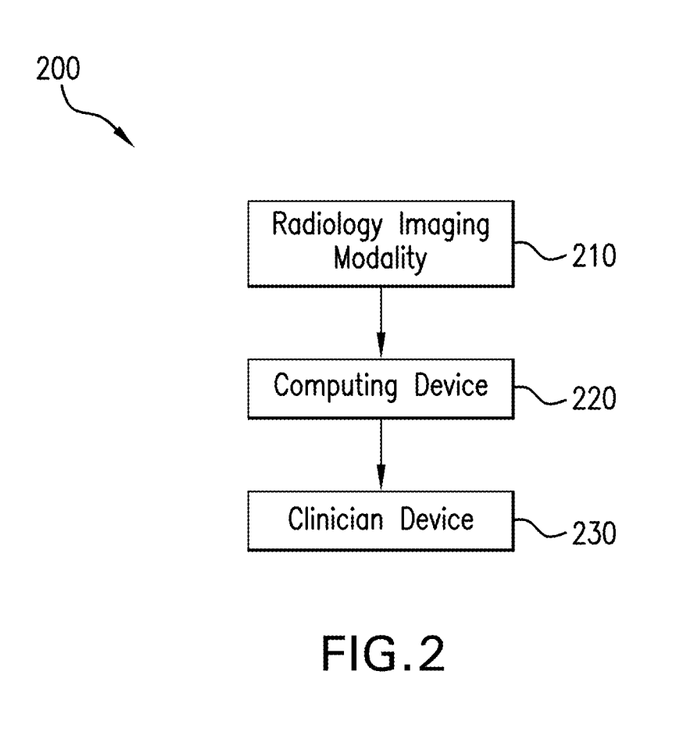
FIG. 2 illustrates an overview of the system for assisting a clinician in identification of perfusion characteristics of an organ.

In an embodiment, FIG. 2 provides an overview of the embodiment as described above, namely, a system for assisting a clinician in identification of perfusion characteristics of an organ as shown by reference numeral 200. With reference to FIG. 2, the steps as disclosed below are implemented by the system which comprises a radiology imaging modality 210, a computing device 220, and a clinician device 230. The clinician device 230 may be the same device as the computing device 220 or it may be a separate device. The clinician device 230 may be, for example, a workstation, a laptop, or a mobile device, which is equipped with a display for viewing visual representations as generated from the computing device 220. Each of the computing device 220 and the clinician device 230 comprise an input means, an output means, a storage means, a connectivity means, and a processor. The output means may include a display. The processor executes a sequence of programmed instructions such as, for example, steps of a process such the process as disclosed herein. The connectivity means may provide a local connection to another device or a remote connection to another device. The computing device 220 may be local or remote with respect to the clinician device 230. The storage means may include content therein such as a database and a computer program.

The process and system as disclosed in the embodiments above may use standard algorithms such as, for example, a region growing algorithm or a shape detection algorithm for segmentation of regions of interest.

While the process and system as disclosed herein are in connection with CMR, those skilled in the art will know that these processing steps may be applied for perfusion characteristic mapping of other imaging modalities such as, without limitation, ultrasound, SPECT and DSE for cardiac imaging, as well as other imaging modalities suited for acquiring time-series image perfusion sequences for biological tissue such as, for example, organs.

1. Acquisition and Pre-processing Steps for Perfusion Analysis

In an embodiment, the first step is the acquisition of a contrast enhanced first-pass perfusion sequence (as represented by reference numeral 110 of FIG. 1) comprising a plurality of two-dimensional image slices and a time series for each of said two-dimensional image slices by using a radiology imaging modality 210, for example, CMR, for contrast-enhanced perfusion imaging of said organ, wherein said plurality of two-dimensional image slices comprises a three-dimensional volume image. The acquired image sequence is such that the imaged organ in each time frame of the perfusion sequence does not change in shape but only changes its signal intensity over the time-series, such that the signal intensity for a particular pixel or voxel is proportionate to the perfusion in the tissue in the region of interest. As used herein, the pixel has two dimensions (2D) and the voxel has three dimensions (3D).

In a related embodiment, the second step (as represented by reference numeral 120 of FIG. 1) is the retrieval of the contrast enhanced first-pass perfusion sequence from the radiology imaging modality 210 such as, for example, CMR, using a computing device 220. The computing device 220 includes network connectivity to enable the retrieval of the image data from the radiology imaging modality 210.

In a related embodiment, the third step (as represented by reference numeral 130 of FIG. 1) is the application of in-plane motion correction to align position of the imaged organ, for example, the heart, using the time series for each of image slices in the perfusion image sequence using the computing device 220. The left ventricular myocardium is seen as a donut in each frame of the two dimensional short axis slice of the perfusion image sequence. Due to respiratory artifacts which may result from the patient's breathing, a motion correction pre-processing step is performed by the computing device 220 which applies a standard algorithm, as is known in the art, for rigid translation plus rotation of the images so that the images of the patient's heart are aligned. This is achieved by applying in-plane motion correction to the organ as depicted at each spatial slice location, using a standard algorithm on the computing device 220 for alignment of said organ in each frame of said time-series of contrast-enhanced two-dimensional perfusion images.

In a related embodiment, the fourth step is that the computing device 220 crops a region of interest (as represented by reference numeral 140 of FIG. 1). In particular, the computing device 220 performs a cropping operation by spatially reducing the volume represented by the series CMR images of the first-pass perfusion sequence, identically in each time-frame of the time-series, down to a smaller interrogation window showing only the organ of interest, for the purpose of creating smaller and more tractable image data for the next processing operations. In particular, this step (as represented by reference numeral 140 of FIG. 1) involves a computing device 220 cropping a region of interest (i.e., a first region of interest) of said contrast-enhanced perfusion images, wherein said first region of interest comprises a first plurality of two dimensional pixels in each slice or three dimensional voxels in the volume image which represents an organ region (i.e., constituted by the plurality of slices that represents the organ at each time-frame).

In a related embodiment, the fifth step is that the computing device 220 performs the following operations on the image data in order to segment out an additional region of interest (as represented by reference numeral 150 of FIG. 1) comprising the region of interest within which perfusion characteristics are required to be analyzed. Each region of interest is a plurality of pixels or voxels which is obtained by applying a standard segmentation algorithm such as a region growing algorithm or a shape detection algorithm, which effectively masks out tissue that is not required to be analyzed and isolates the tissue region for perfusion analysis.

In one example, the detection of the left ventricular (LV) myocardium from short-axis image slices of the heart may be achieved automatically by a sequence of steps operating on an image volume constituted by two-dimensional slice images at a single time frame, that together amounts to shape detection, may be achieved as follows: a) automatically detecting the LV myocardium midline for each image slice in the perfusion sequence by applying a standard line-thinning algorithm, known in the art, operating on a binary thresholded version of the image data, b) identifying the centroid and radius of the LV myocardium mid-line by using a Circular Hough Transform that iteratively operates on each resulting pixel point or voxel from the LV myocardium midline, c) using a canny edge detection algorithm to mark the endocardium (inner myocardial wall) and epicardium (outer myocardial wall) of the LV myocardium and subsequently calculating the average distance between the centroid and the circumferential points for each cardiac perfusion MRI slice in order to identify the mean LV myocardial wall thickness, and d) scaling the detected LV myocardial mid-line from the detected centroid, using the identified wall thickness information in the previous step, in order to demarcate the endocardium using a circular shape approximation, with set radial tolerance limits to limit the inclusion of pixel data or voxel data from outside the LV myocardium into the region of interest in each image slice.

In a related embodiment, the sixth step is to subdivide the region of interest from step five into arbitrarily shaped sub-regions of interest (i.e., additional regions of interest) within which signal intensity data is evaluated as an average intensities of pixels or voxels. In one example, for the LV myocardium as seen in short-axis image slices of the heart, the sub-region of interest comprises of several radial sectors identified in a regular clockwise or anticlockwise fashion from the identified centroid location. As per American Heart Association (AHA) convention, the LV myocardium as seen in the mid-ventricular slice level may be subdivided into six radial sectors of 60° each starting with the anterior interventricular septum.

2. Perfusion Analysis

Figure 3:
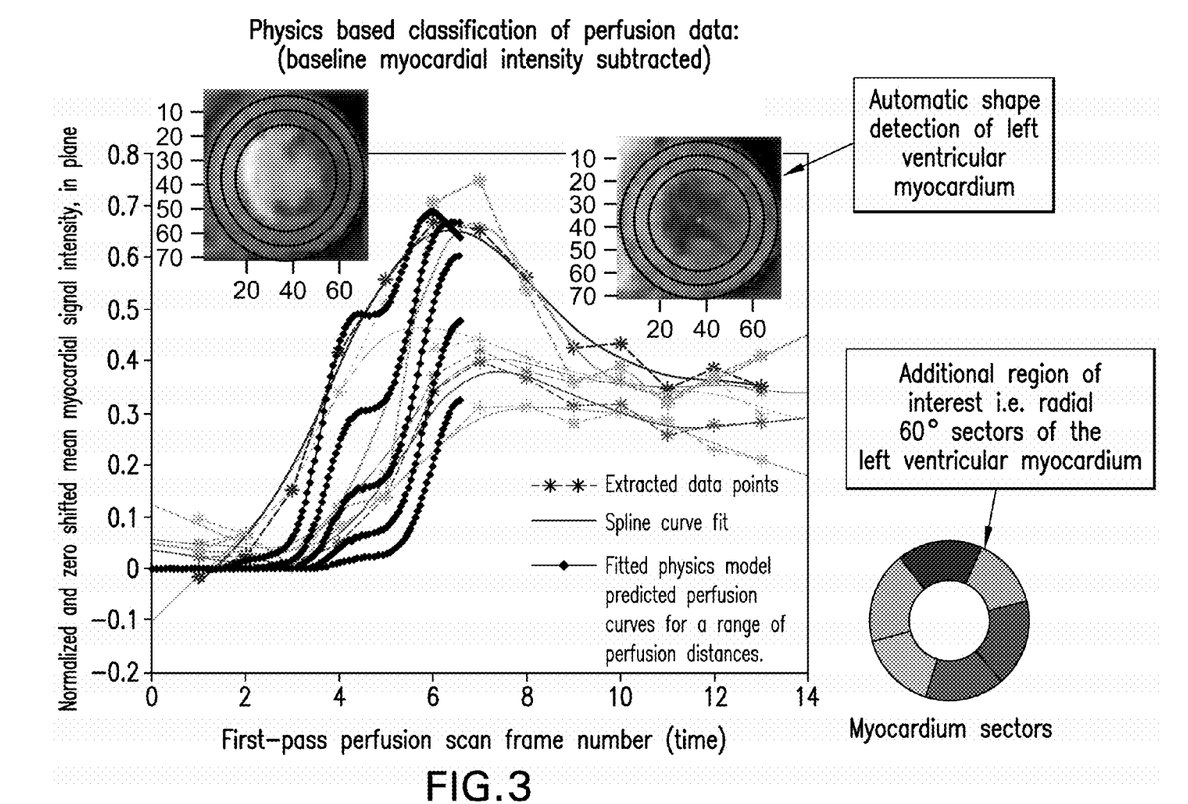
FIG. 3 illustrates a visual representation of observed perfusion uptake curves of contrast agent in a patient compared to expected normal perfusion uptake curves.

In an embodiment, the first step in the perfusion analysis is preliminary perfusion quantification. A computing device 220 performs the preliminary perfusion quantification by determining an average of signal intensities for pixels or voxels in each of the six radial sectors of the LV myocardium or other additional regions of interest (as described previously in the section for describing the acquisition and pre-processing steps for perfusion analysis). In this manner, perfusion rise curves are calculated by the computing device 220 based upon the observed perfusion uptake curves of the contrast agent as determined by the relative signal intensity over time for each slice in the perfusion sequence. The computing device 220 then displays a visual representation of the observed perfusion uptake curves in the six radial sectors for each slice in the perfusion sequence. FIG. 3 shows a physics based classification of perfusion data: (baseline myocardial intensity subtracted). In particular, FIG. 3 depicts a comparison of the observed perfusion uptake curves in the six radial 60° sectors for each slice in the perfusion sequence against expected normal perfusion uptake curves computed by applying physics-based image processing technique for perfusion, namely a patient-specific numerical advection-diffusion blood transport model. (FIG. 3 shows a legend which depicts the myocardium sectors, namely, the additional region of interest (i.e., as represented by radial 60° sectors of the left ventricular myocardium.)) As also shown in FIG. 3, along the y axis, normalized and zero shifted mean myocardial signal intensity in plane is plotted against the number of frames in the perfusion sequence along the "x" axis. As described by the legend and as shown by the plotted lines, FIG. 3 shows extracted data points which reflect the observed perfusion uptake curves, expected normal perfusion uptake curves (i.e., the fitted physics model predicted curves for a range of perfusion distances), and a spline curve fit of the expected normal perfusion uptake curves to the observed perfusion uptake curves. As shown in FIG. 3, automatic shape detection is shown of left ventricular myocardium using a circular shape approximation for the endocardial and epicardial LV walls in a two-dimensional short-axis slice of the heart.

In an embodiment, the second step in the perfusion analysis is that the perfusion uptake curves from the patient's perfusion data (as described above) is compared against the perfusion rise curves which are expected based upon the application of the physics-based image processing technique, namely, the patient-specific numerical advection-diffusion blood transport model for expected normal perfusion as explained in more detail below.

In an embodiment, the third step (as represented by reference numeral 160 of FIG. 1) in the perfusion analysis is that the six radial sectors of the additional regions of interest are classified according to whether there are perfusion defects within the LV myocardium which may indicate the existence of normal or at-risk tissue (i.e., ischemic tissue) using an analytical curve fitting technique. This is explained in more detail below in the section describing the analytical diffusion parameter-based pixel or voxel ranking model section.

In an embodiment, the fourth step in the perfusion analysis is that the regions of poor perfusion uptake (as determined n the previous step) are analyzed at the pixel level or voxel level for a region of interest by the computing device 220 upon application of the residence time index model as described in more detail in the section below. (This is also represented by reference numeral 160 of FIG. 1.)

Figure 4A:
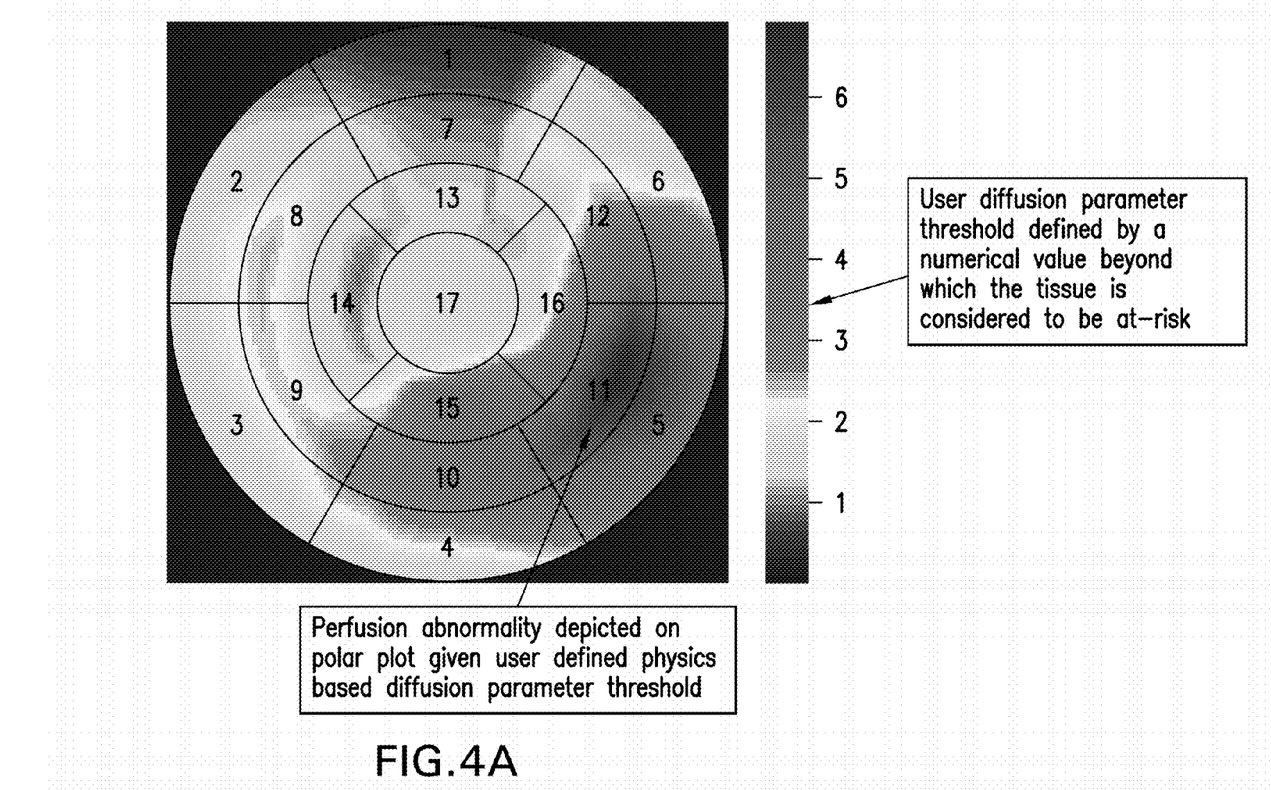
FIG. 4A illustrates a visual representation resulting from the application of the analytical diffusion parameter-based pixel or voxel ranking model and a user defined physics based diffusion parameter threshold to perfusion characterization in the left ventricular myocardium; in addition, a standardized American Heart Association model polar plot is superimposed as an aid for interpretation of the visual representation.

As an example, FIG. 4A illustrates a visual representation resulting from the application of the analytical diffusion parameter-based pixel or voxel ranking model for the same short axis slice as shown on a computing device 220; the standardized American Heart Association polar plot is superimposed over the visual representation as an aid in interpretation. To the right of the visual representation is a bar which represents a user-defined threshold for the diffusion parameter which is defined by a numerical value beyond which the tissue is considered to be at-risk. Based upon this user-defined threshold, perfusion abnormality is depicted on the polar plot given the threshold. As shown in the example of FIG. 4A, perfusion abnormality is primarily depicted in region numbers 4, 5, 6, 10, 11, 12, 15, 16. Regions with high diffusion parameter indices (as shown by darkly shaded regions in FIG. 4A) are considered ischemic.

Each of the physics-based image processing techniques is explained in more detail in the following sections. These physics-based image processing techniques are used in classifying the perfusion characteristics of the additional region or additional regions of interest by characterizing a plurality of observed perfusion uptake curves for the additional region(s) of interest by applying at least one physics-based image processing technique (as represented by reference numeral 160 of FIG. 1) for producing at least one perfusion characteristics map of the perfusion characteristics using user-defined or default criteria. The perfusion characteristics map displays regions of at-risk and normal perfusion tissue. The computing device 220 displays the perfusion characteristics map and this map is displayed on the clinician device 230 (as represented by reference numeral 170 of FIG. 1).

a. Numerical Approach—Patient-Specific Numerical Advection-Diffusion Blood Transport Model for Expected Normal Perfusion The first physics based perfusion characterization technique is one that involves the comparison of observed perfusion uptake curves against expected normal perfusion uptake curves describing expected normal perfusion uptake. The expected normal perfusion uptake curves result from the application of this patient-specific numerical advection-diffusion blood transport model for expected normal perfusion. Therefore, a 1D spatial model for normal myocardial perfusion over time, namely, a patient-specific numerical advection-diffusion blood transport model for expected normal perfusion in the heart, is described in this section. This model uses a normalized patient specific physiological cardiac output flow waveform obtained by assuming proportionality to extracted wall thickening data measured from cine CMR image sequences of the patient's heart. This waveform estimates input transient advection velocity of the contrast agent, u, in equation (1) which is the advection-diffusion partial differential transport equation employed to model blood perfusion. The computing device 220 uses the numerical solution to a one dimensional (1D) spatial version of the advection-diffusion transport equation in order to determine the temporal change in contrast agent intensity, C, which is proportionate to the contrast agent uptake, and therefore generate expected normal perfusion uptake curves at different spatial locations downstream from the starting location of the modeled 1D space (i.e., x=0) symbolic of the left ventricular blood pool, assuming an initial (i.e., at time, t=0) contrast agent spatial distribution at this location. In one example, the initial contrast agent spatial distribution in the 1D spatial dimension is modeled by equation (2).

The advection and diffusion of contrast agent intensity, $C(x, t)$, from the LV myocardium blood pool to the myocardium is simulated using a transient 1D transport model that represents the transport of an initial concentration of contrast agent, $C_0(x, t=0)$, from blood pool to myocardium via the coronary arteries, as a 1D distance, x. The transport model has two parameter inputs: 1) characteristic diffusion coefficient, D, (as used herein, references to "diffusion parameter" is synonymous with characteristic diffusion coefficient) and 2) advection velocity, u, and is defined by the following equation (which is referred to herein as also a 1D heat diffusion equation):

$$\frac{dC}{dt} = D\nabla^2 C - \nabla \cdot (uC) \qquad (1)$$

As discussed above, the patient-specific numerical advection-diffusion blood transport model for expected normal perfusion estimates the input transient advection velocity using averaged and normalized patient-specific physiological waveforms obtained from the extracted wall thickening data (as described previously) measured from cine CMR scan sequences of the patient's heart. This is based on the assumption of an inherent proportionality between wall thickening and the rate of myocardial perfusion for a normal cardiac muscle. The analytical solution for equation (1) exists for a constant advection velocity, as a boundary value problem, given initial conditions, namely, the initial concentration of the contrast agent (i.e., $C(x, t=0)$). However, in the case of the heart, pulsatile cardiac output conditions render the advection velocity as a temporally varying quantity and the initial intensity is not a point source but a distribution over the LV blood pool. The latter may be considered as distribution of concentration over in the spatial dimensions—i.e., over the 1D space $a \leq x \leq b$, where a, b are constants representing the 1D distance along which an initial concentration of contrast agent is located. The initial distribution of concentration over in the spatial dimension implies a condition such as the following, for a small finite extent of the normalized 1D space, for example over $-1 < x < -0.8$, if a=-1 and b=1 defines the net extent of the 1D space as shown by the following equation:

$$C_0(x, t=0) = 1 - (10(x+1)-1) \qquad (2)$$

In order to consider pulsatile perfusion in a one dimensional spatial model of myocardial perfusion over time, a numerical solution is necessary. Constant flux type spatial boundary conditions are applied after solution initialization, during the numerical solution process. A numerical solver routine employing an implicit time integration scheme along with second order finite differencing in space, both as known in the art, is used in order to solve for the new spatial distribution of contrast agent at the end of every time step. Other fully implicit or semi-implicit numerical time integration schemes as known in the art may alternately be employed for this solver. The physics model is made patient specific by iteratively scaling: a) the normalized advection velocity input waveform in order to match the mean perfusion uptake time of the patient-specific numerical advection-diffusion blood transport model for expected normal perfusion to the quantified perfusion uptake from first-pass perfusion CMR scans (preferably acquired under stress conditions); and b) the characteristic diffusion coefficient, D, of the patient-specific numerical advection-diffusion blood transport model for expected normal perfusion to match the attenuation in pixel-averaged or voxel-averaged peak perfusate intensity observed in the myocardium at peak uptake when compared to that in the LV blood pool. In order to meet the requirements of the above criteria, the Peclet number (Pe) was used as a reference to relate D and the mean value of pulsatile advection velocity, u. For Pe$\gg$1, diffusion is dominant and the initial contrast agent distribution spreads out faster than it moves downstream, characteristic of perfusion by microvasculature; and for Pe$\ll$1, advection is dominant and the distribution of contrast agent moves downstream faster than it spreads out, characteristic of perfusion in larger coronary vessels. In this manner, a single model is used to describe the perfusion conditions for the entire myocardial region by considering differing distances of perfusate transport along the arbitrary 1D space, in order to match the quantified first-pass perfusion uptake curves to the best possible extent. Model generated expected normal curves at different locations downstream from the location of the initial contrast agent spatial distribution are matched to the perfusion uptake curves extracted from CMR images. The fall of the perfusion curves (i.e., indicated by diminishing signal intensity) in the observed perfusion uptake curves is influenced by recirculation of the contrast agent and hence does not match the constant initial spatial distribution driven physics model for contrast agent transport. Therefore, only perfusion uptake is compared with observed perfusion uptake curves from patient images. This analysis is recommended to be performed at level of myocardial sectors or regions of interest only and not at the pixel-level or voxel-level due to computational costs of the numerical algorithm.

In an embodiment, the clinician classifies the observed perfusion uptake curves depicting perfusion characteristics (i.e., based on flow from the LV into the myocardium) by visually comparing the observed perfusion uptake curves against at least one expected normal perfusion uptake curve obtained from a physics-based image processing technique, namely, the patient-specific numerical advection-diffusion blood transport model for expected normal perfusion in the organ. In this manner, the clinician may determine how far the observed perfusion uptake curves are from any one expected perfusion uptake curve.

In an alternate embodiment of the second step, the computing device 220 displays the visual representation of the perfusion characteristics (i.e., a perfusion characteristics map) of the organ (as represented by reference numeral 170 of FIG. 1). The visual representation is a color map of the perfusion characteristics. The color map highlights the closeness of matching the observed perfusion uptake curves (i.e., based on flow from the LV into the myocardium) to at least one expected normal perfusion uptake curve obtained from the physics-based image processing technique, namely, the patient-specific numerical advection-diffusion blood transport model for expected normal perfusion in said organ, using at least one standard error estimation method. In this manner, the clinician may determine how far the observed perfusion uptake curves are from any one expected perfusion uptake curve. An example of one standard error estimation method is a root-mean-square error method.

FIG. 3 shows an example of such a visual representation of an observed perfusion uptake curve of contrast agent in a patient (i.e., based on flow from the LV into the myocardium) compared to a expected normal perfusion uptake curve.

b. Analytical Approach for Quantitative Spatial Mapping of Entire LV Myocardium—Diffusion Parameter Based Pixel or Voxel Ranking In an embodiment, using the results from the patient-specific numerical advection-diffusion blood transport model for expected normal perfusion, myocardial sectors that are under suspicion of containing ischemic tissue may be investigated at a pixel or a voxel for a region of interest using the diffusion parameter based pixel or voxel ranking model described in this section.

In an embodiment, a region of interest is classified as either normal tissue or at-risk tissue (as represented by reference numeral 160 of FIG. 1) using a threshold comprising a range of values for said characteristic diffusion coefficient of said normal tissue, wherein said threshold is either a user-defined threshold or a predetermined threshold. In a related embodiment, a user-defined threshold is comprised of user-defined diffusion parameter intervals for normal and at-risk tissue. In another related embodiment, a predetermined threshold is comprised of diffusion parameter intervals for normal and at-risk tissue, as determined based on statistical inferences drawn from patient data analyzed using the same fitting technique.

In an embodiment, a plurality of characteristic diffusion coefficients are calculated fir the plurality of pixels or voxels within the region of interest using the image-based physics model as disclosed in this section.

In an embodiment, non-linear least-squares curve fitting of a physics-based analytical expression for the solution to a transport equation describing perfusion by advection and diffusion of blood for constant advection velocity (i.e., expected normal perfusion uptake curves) to the perfusion uptake data for observed region(s) of interest (i.e., observed perfusion uptake curves) for the region of interest. This step results in a characteristic diffusion coefficient, D, for each observed pixel or voxel for the region of interest (which may be in two dimensions (2D) or three dimensions (3D)).

Figure 4B:
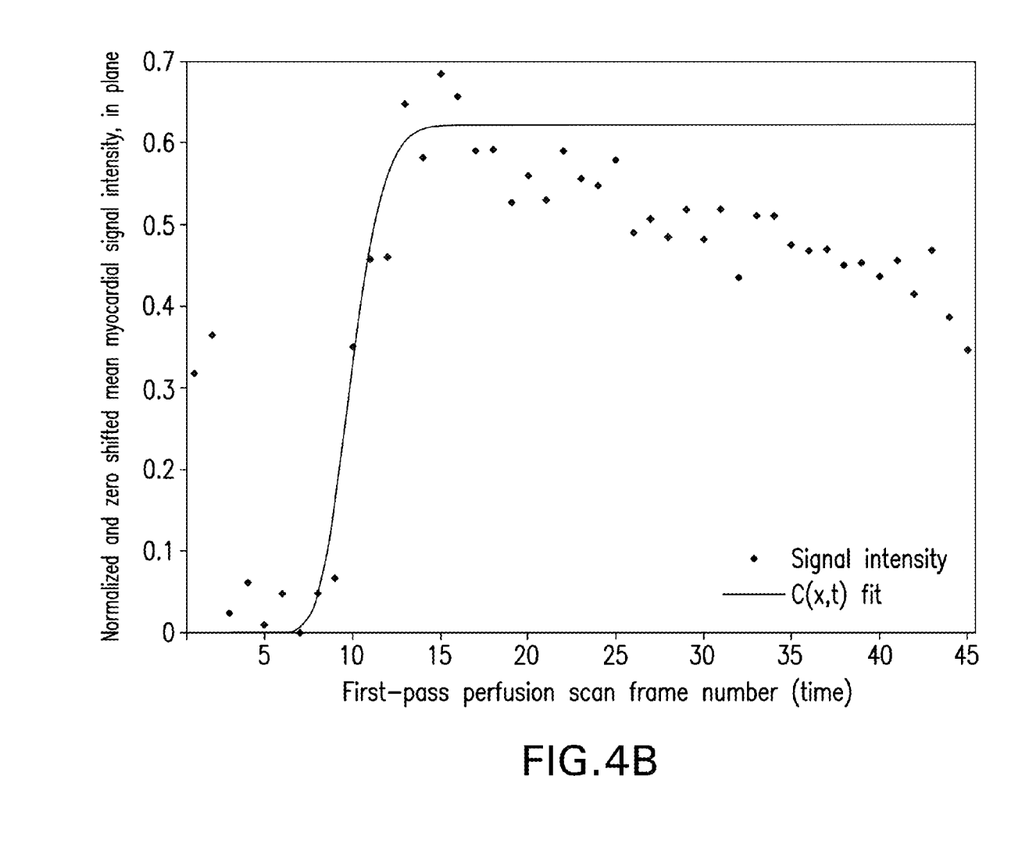
FIG. 4B shows an observed perfusion uptake curve fit of time to signal intensity by applying the analytical diffusion parameter-based pixel or voxel ranking model.

In an embodiment, the curve fit of this analytical diffusion parameter based pixel or voxel ranking model resembles a sigmoid function. As an example, as shown in FIG. 4B, first-pass perfusion scan frame number (time) (along the x axis) is plotted against normalized and zero shifted mean myocardial signal intensity, in plane (along the y axis). Each first-pass perfusion scan frame is a time frame. The dots represent signal intensity of the observed perfusion uptake curves and the curve fit line (i.e., C(x,t) fit) represents the time variation of concentration of contrast agent using equation (3). The observed perfusion uptake curve (as shown in FIG. 4B) comprises points of signal intensity for a time series (i.e., time evolution) which is observed for a pixel or voxel for the region of interest. This is the result of applying the analytical diffusion parameter based pixel or voxel ranking model. In the manner as exemplified by FIG. 4B, regions of interest are classified according to normal tissue or at-risk tissue (i.e., ischemic tissue).

In an embodiment, a computing device 220 displays the visual representation of the perfusion characteristics of the organ, wherein the visual representation is a color map of the perfusion characteristics (i.e., a perfusion characteristics map) (as represented by reference numeral 170 of FIG. 1). This color map highlights normal tissue and at-risk tissue (i.e., ischemic tissue). The region of interest is classified as being normal or at-risk using user-defined criteria or default criteria for the perfusion characteristics.

This diffusion based parameter index pixel or voxel ranking model is a physical characterization index for pixel-level or voxel-level for the region of interest. The diffusion parameter indices for tissue perfusion in patients analyzed using this technique correlate with a probabilistic estimate for extent of stenosis to expect in a coronary vessel that perfuses the tissue territory occupied by the pixel or voxel for the region of interest characterized by the diffusion parameter index, the relational data for which is stored in a training patient database which the computing device 220 accesses in order to classify regions of at-risk and normal tissue (as represented by reference numeral 160 of FIG. 1). In this manner, an absolute physical meaning of the diffusion parameter based pixel or voxel ranking is obtained for the region of interest which in-turn form the basis for the default (i.e., predetermined) or user-defined thresholds for classifying spatial extents of at-risk tissue.

The advection-diffusion transport of a concentration of contrast agent, C, which is transported along two orthogonal spatial directions, x as well as say y, was solved by Jha et al. considering a constant initial concentration upstream at a plane through x=0, y=0 at some initial time t=0. See B. K. Jha, N. Adlakha, M. N. Mehta, Analytic solution of two dimensional advection diffusion equation arising in cytosolic calcium concentration distribution, Int. Math. Forum, Vol. 7, 2012, no. 1-4, 135-144. This analytical solution is obtained by this technique after applying suitable parametric substitutions to the independent variables of the transport equation so they individually represent a position in 2D space and the diffusion based parameter itself now represents a formulation that includes characteristic diffusion coefficients in the two orthogonal spatial dimensions. An analytical expression that is concordant with the nature this solution is used in order to fit the observed perfusion uptake data based upon signal intensity over time:

$$C(x, t) = a \, \text{erfc}\left(\frac{x + Ut}{\sqrt{Dt}}\right) + b \, \text{erfc}\left(\frac{x - Ut}{\sqrt{Dt}}\right) \quad (3)$$

where: a, b are an arbitrary positive constants that determine the quality of the fit, D is a positive real number indicating the diffusion transport coefficient, x is the 1D spatial variable, U is the mean positive velocity of flow and erfc represents the complementary error function. C(x,t) here is a dependent variable representing concentration of Gadolinium contrast agent seen in the image plane represented spatially by its distance from the left ventricular blood pool by variables, x, and time, t. The unknown in this equation for the purpose of curve fitting to the observed perfusion uptake curves in the selected region of interest is the parameter, D, or the diffusion based parameter. Solutions to the complementary error function (i.e., erfc in equation (3)) are generally found in tables or as built-in functions in a spreadsheet or computer programming language and so this model becomes a convenient means of representing the perfusion uptake curves for each pixel or voxel of the region of interest in the myocardium by a single number (i.e., the characteristic diffusion coefficient, D). For each CMR image slice level, a unique set of parameters comprising x, U, a and b are determined based upon curve fitting to the mean time-signal intensity observed perfusion uptake data of the region interest obtained from first pass perfusion CMR images for each analyzed image slice level. These slice-specific constants are utilized to determine the diffusion parameter, D, for each pixel or voxel for the region of interest in that slice, which may be compared locally with the D obtained from the mean time-signal intensity of the region of interest for observed perfusion uptake for that slice, globally with the D obtained from the slices across the entire left ventricular myocardium.

c. Residence Time Index

The third perfusion characterization and classification method characterizes the observed perfusion uptake curves for the region of interest by a residence time index. The residence time index highlights the number of consecutive time-frames for which the signal intensity in the regions of interest lies below a user-defined threshold. Consecutive frames of the first-pass perfusion CMR image sequences are usually separated by at least one cardiac cycle, and therefore pixels or voxels remaining within user-defined low intensity tolerance threshold for two or more consecutive frames are considered as likely perfusion abnormalities. Therefore, a second user-defined magnitude of residence-time is employed in order to classify the observed perfusion uptake regions of interest as being normal or at-risk. Pixels or voxels with signal intensity values lying below the set intensity tolerance threshold for two consecutive frames were considered to have a residence time of one unit. This residence time index is incremented and accounted for throughout the perfusion uptake time-series in order to guide spatial identification of contiguous pixels or voxels with the low perfusion.

In an embodiment, a use-defined threshold defines a range of intensity values of a plurality of pixels or voxels of the region of interest. By adjusting a user-defined threshold of signal intensities of pixels or voxels of regions of interest for a given myocardial slice, the residence time index is used to accentuate the presence of ischemic regions. Increasing the user-defined threshold may lead to increased sensitivity for detection of ischemic myocardium. In this manner, local intensity distribution statistics may be utilized in order to limit the impact of visual noise on the fitted parameters. The residence time index is a means for quantitatively identifying local perfusion defects in the manner that the human eye inspects the first-pass perfusion CMR time-series, in every image slice of the left ventricular myocardium. A more physical characterization index for pixel-wise or voxel-wise perfusion uptake is however the diffusion index as described in the analytical diffusion parameter-based pixel or voxel ranking model. However, this model may be adopted to quickly investigate observed perfusion uptake at the pixel or voxel level in order to identify the region of interest the contiguous groups of pixels or voxels that show defective perfusion characteristics within a myocardial region suspected of containing ischemic tissue (i.e., at risk tissue in the region of interest).

In one embodiment, pixels or voxels with intensity values lying within the user-defined low intensity tolerance threshold for two or more consecutive frames are considered to have a residence time of one unit.

In an embodiment, a technique is established in order to characterize pixels or voxels demonstrating low perfusion, as a relative measure to highlight local perfusion defects, in comparison with normal pixels or voxels in the same field of view.

In an embodiment, the residence time index is then incremented and accounted for throughout the perfusion sequence in order to guide spatial identification of contiguous pixels or voxels with the low perfusion.

In an embodiment, a computing device 220 computes a residence time index by determining the number of consecutive time frames of said two-dimensional image slices having intensity values less than said intensity value for indication of at-risk tissue using said physics-based image processing technique, wherein said physics-based image processing technique is a residence time index model. (This is represented by reference numeral 160 in that perfusion characteristics of additional regions of interest are classified.)

In an embodiment, the computing device 220 displays the visual representation of the perfusion characteristics of the organ (as represented by reference numeral 170 of FIG. 1). The visual representation is a color map of said perfusion characteristics (i.e., a perfusion characteristics map). The color map highlights said residence time index. The color map is created based upon this physics model characterizes and ranks the entire LV myocardial region (i.e., not just infarcted or high risk myocardium).

The above disclosure presents examples of available embodiments of the present invention. Those skilled in the art will readily observe that numerous other modifications and alterations may be made without departing from the spirit and scope of the invention. Accordingly, the above disclosure is not intended as limiting and the appended claims are to be interpreted as encompassing the entire scope of the invention.

What is claimed is:

1. A method, implemented via a computing device, for generating a characteristic map of perfusion characteristics of cardiac tissue from at least one radiology image comprising the steps of:
   a. Retrieving a contrast-enhanced perfusion sequence using a computing device, wherein said perfusion sequence is generated using a radiology imaging modality and wherein said perfusion sequence comprises:
      a plurality of two-dimensional image slices comprising a three-dimensional volume image and
      a time series for each of said two-dimensional image slices, and
   wherein each pixel or voxel of each two-dimensional image slice comprises a signal intensity proportional to perfusion at that location in the cardiac tissue;
   b. Applying in-plane motion correction using said computing device to align position of the cardiac tissue using said time series for each of said image slices;
   c. Cropping a first region of interest of said contrast-enhanced perfusion images using said computing device, wherein said first region of interest comprises a first plurality of pixels or voxels;

d. Segmenting out at least one additional region of interest from said first region of interest, wherein said additional region of interest comprises a second plurality of pixels or voxels and wherein said segmenting is further achieved by applying a shape detection algorithm comprising the steps of:
   detecting a mid-line of the left ventricular myocardium for each two-dimensional image slice,
   identifying a centroid and a radius of the left ventricular myocardium mid-line using a Circular High Transform, wherein the Circular High Transform iteratively operates on each resulting pixel or voxel corresponding to the left ventricular myocardium mid-line,
   identifying a mean left ventricular myocardial wall thickness by applying a canny edge detection algorithm to thereby mark the endocardium and the epicardium of the left ventricular myocardium and calculate an average distance between the centroid and a plurality of circumferential points for each two-dimensional image slice,
   scaling the detected left ventricular myocardial mid-line from the detected centroid using the identified wall thickness to thereby demarcate the endocardium using a circular shape approximation, wherein the circular shape approximation further comprises at least one radial tolerance limit to thereby exclude pixel data or voxel data corresponding to regions outside of the left ventricular myocardium from the region of interest in each two-dimensional image slice;
e. generating at least one characteristic map of said perfusion characteristics using a computing device, wherein the characteristic map defines at-risk and normal perfusion areas, wherein generating further comprises:
   subdividing each region of interest into a plurality of subregions,
   generating at least one expected normal perfusion update curve by applying a physics-based image processing technique, wherein the physics-based image processing technique further comprises a patient-specific numerical advection diffusion blood transport model, and
   comparing, using a computing device, a plurality of observed perfusion uptake curves with at least one expected normal perfusion uptake curve to thereby generate the characteristic map of perfusion characteristics for at least one of said subregions;
   identifying at least one subregion comprising at least one at risk perfusion area,
   applying at least one physics-based image processing technique to at least one pixel or voxel in at least one at risk region of interest to confirm the perfusion characteristic of the pixel or voxel as comprising at least one of: a normal perfusion area and an at risk perfusion area; and
f. Displaying at least one visual representation of said perfusion characteristics of the portion of the heart on a clinician device for review by said clinician to thereby enable the clinician in generating at least one diagnosis based on the perfusion characteristics, wherein said visual representation is a two-dimensional visual representation or a three-dimensional visual representation and further comprises a color map, wherein said color map is representative of the matching of observed perfusion uptake curves to at least one modeled normal perfusion uptake curve obtained from the a patient-specific numerical advection-diffusion blood transport model using at least one standard estimation method, and wherein said displaying further comprises superimposing a polar plot over the visual representation.

2. The method of claim 1 wherein said one standard estimation method is a root-mean-square error method.

3. The method of claim 1 wherein comparing the observed perfusion uptake curves with at least one expected normal perfusion uptake curve further comprises applying at least one curve fitting technique to thereby calculate a characteristic diffusion coefficient for said second plurality of pixels or voxels of each additional region of interest.

4. The method of claim 3 wherein said curve fitting method is a non-linear least squares curve fitting method.

5. The method of claim 1 wherein said additional region of interest is further classified as either normal tissue or at-risk tissue using a threshold comprising a range of values for said characteristic diffusion coefficient of said normal tissue, wherein said threshold is either a user-defined threshold or a predetermined threshold.

6. The method of claim 5 wherein said user-defined threshold defines a range of signal intensity values of pixels or voxels of said additional region of interest and wherein said additional region of interest is classified as at-risk tissue if an average value of said second plurality of pixels or voxels of said additional region of interest is below said user-defined threshold for a user-defined number of time frames.

7. The method of claim 6 wherein said computing device further applies a residence time index model to compute a residence time index of said additional region of interest by determining the number of consecutive time frames of said two-dimensional image slices having signal intensity values less than said signal intensity value for indication of at-risk tissue.

8. The method of claim 7 wherein said computing device displays said visual representation of said perfusion characteristics of said additional region of interest, wherein said visual representation is a color map of said perfusion characteristics, wherein said color map highlights said residence time index.

9. The method of claim 7 further comprising applying said residence time index to identify at least one plurality of contiguous pixels or voxels corresponding to at risk areas in said organ.

10. The method of claim 1 wherein said clinician device is said computing device.

11. The method of claim 1 wherein said clinician device is local to said computing device.

12. The method of claim 1 wherein said clinician device is remote to said computing device.

13. The method of claim 1 wherein said computing device is deployed in a local environment.

14. The method of claim 1 wherein said computing device is deployed in a cloud computing environment.

15. The method of claim 1 wherein said computing device is deployed in a hosted environment.

16. The method of claim 1 wherein characterizing a plurality of observed perfusion uptake curves further comprises:
   generating an average of signal intensities for pixels or voxels in at least one of said subregions,
   calculating a plurality of observed perfusion uptake curves for each said subregion based on said average signal intensity,
   applying at least one physics-based image processing technique to generate a normal perfusion curve,
   comparing said observed perfusion uptake curves to at least one normal perfusion curve to generate a characteristic map of perfusion characteristics in each said subregion, wherein said characteristic map comprises at least one of: a normal perfusion area and an at risk perfusion area.

17. A system for assisting a clinician in generating at least one diagnosis of cardiac tissue by generating a characteristic map of perfusion characteristics of the cardiac tissue from at least one radiology image, comprising:
- a radiology imaging modality acquires a contrast-enhanced perfusion sequence which comprises a plurality of two-dimensional image slices and a time series for each of said two-dimensional image slices by using the radiology imaging modality for contrast-enhanced perfusion imaging of said cardiac tissue, wherein said plurality of two-dimensional image slices comprises a three-dimensional volume image and wherein each pixel or voxel of said two-dimensional image slice comprises a signal intensity proportional to perfusion at that location in the cardiac tissue; and
- a computing device configured for:
  - a. retrieving said perfusion sequence from said radiology imaging modality,
  - b. applying in-plane motion correction using said computing device to align the position of said cardiac tissue using said time series for each of said image slices,
  - c. cropping a first region of interest of said contrast-enhanced perfusion images, wherein said first region of interest comprises a first plurality of pixels or voxels,
  - d. segmenting out at least one additional region of interest from said first region of interest wherein said additional region of interest comprises a second plurality of pixels or voxels and wherein said segmenting is further achieved by applying a shape detection algorithm, comprising:
    - detecting a mid-line of the left ventricular myocardium for each two-dimensional image slice,
    - identifying a centroid and a radius of the left ventricular myocardium mid-line using a Circular High Transform, wherein the Circular High Transform iteratively operates on each resulting pixel or voxel corresponding to the left ventricular myocardium mid-line,
    - identifying a mean left ventricular myocardial wall thickness by applying a canny edge detection algorithm to thereby mark the endocardium and the epicardium of the left ventricular myocardium and calculate an average distance between the centroid and a plurality of circumferential points for each two-dimensional image slice,
    - scaling the detected left ventricular myocardial mid-line from the detected centroid using the identified wall thickness to thereby demarcate the endocardium using a circular shape approximation, wherein the circular shape approximation further comprises at least one radial tolerance limit to thereby exclude pixel data or voxel data corresponding to regions outside of the left ventricular myocardium from the region of interest in each two-dimensional image slice, and
  - e. generating at least one characteristic map of said perfusion characteristics using said computing device, wherein the characteristic map defines at-risk and normal perfusion areas and, wherein generating the characteristic map further comprises:
    - subdividing each region of interest into a plurality of subregions,
    - generating at least one expected normal perfusion uptake curve by applying a physics-based image processing technique, wherein the physics-based image processing technique further comprises a patient-specific numerical advection diffusion blood transport model, and
    - comparing, using said computing device, a plurality of observed perfusion uptake curves with at least one expected normal perfusion uptake curve to thereby generate the characteristic map of perfusion characteristics for at least one of said subregions,
    - identifying at least one subregion comprising at least one at risk perfusion area,
    - applying at least one physics-based image processing technique to at least one pixel or voxel in at least one identified at-risk subregion to confirm the perfusion characteristic of the pixel or voxel as comprising at least one of: a normal perfusion area and an at risk perfusion area, and
    - displaying at least one visual representation of said perfusion characteristics of the portion of the heart on a clinician device for review by said clinician to thereby enable the clinician in generating at least one diagnosis based on the perfusion characteristics, wherein said visual representation is a two-dimensional visual representation or a three-dimensional visual representation and further comprises a color map, wherein said color map is representative of the matching of observed perfusion uptake curves to at least one modeled normal perfusion uptake curve obtained from a patient-specific numerical advection-diffusion blood transport model using at least one standard estimation method, and wherein said displaying further comprises superimposing a polar plot over the visual representation.

18. The system of claim 17 wherein said one standard estimation method is a root-mean-square error method.

19. The system of claim 17 wherein comparing the observed perfusion uptake curves with at least one expected normal perfusion uptake curve further comprises applying at least one curve fitting technique to thereby calculate a characteristic diffusion coefficient for said second plurality of pixels or voxels of each additional region of interest.

20. The system of claim 19 wherein said curve fitting method is a non-linear least squares curve fitting method.

21. The system of claim 17 wherein said additional region of interest is further classified as either normal tissue or at-risk tissue using a threshold comprising a range of values for said characteristic diffusion coefficient of said normal tissue, wherein said threshold is either a user-defined threshold or a predetermined threshold.

22. The system of claim 21 wherein said user-defined threshold defines a range of signal intensity values of pixels or voxels of said additional region of interest and wherein said additional region of interest is classified as at-risk tissue if an average value of said second plurality of pixels or voxels of said additional region of interest is below said user-defined threshold for a user-defined number of time frames.

23. The system of claim 22 wherein said computing device further applies a residence time index model to compute a residence time index of said additional region of interest by determining the number of consecutive time frames of said two-dimensional image slices having signal intensity values less than said signal intensity value for indication of at-risk tissue.

24. The system of claim 23 wherein said computing device displays said visual representation of said perfusion characteristics of said additional region of interest, wherein said visual representation is a color map of said perfusion characteristics, wherein said color map highlights said residence time index.

25. The system of claim 17 wherein said clinician device is said computing device.

26. The system of claim 17 wherein said clinician device is local to said computing device.

27. The system of claim 17 wherein said clinician device is remote to said computing device.

28. The system of claim 17 wherein said computing device is deployed in a local environment.

29. The system of claim 17 wherein said computing device is deployed in a cloud computing environment.

30. The system of claim 17 wherein said computing device is deployed in a hosted environment.

* * * * *